United States Patent [19]
Toth

[11] Patent Number: 5,457,724
[45] Date of Patent: Oct. 10, 1995

[54] AUTOMATIC FIELD OF VIEW AND PATIENT CENTERING DETERMINATION FROM PRESCAN SCOUT DATA

[75] Inventor: Thomas L. Toth, Brookfield, Wis.

[73] Assignee: General Electric Company, Milwaukee, Wis.

[21] Appl. No.: 252,863

[22] Filed: Jun. 2, 1994

[51] Int. Cl.⁶ .................................................. A61B 6/02
[52] U.S. Cl. .................................. 378/4; 378/98; 378/205
[58] Field of Search ......................... 378/4, 15, 20, 378/98, 98.2, 98.7, 901, 205

[56] References Cited

U.S. PATENT DOCUMENTS 5,034,969  7/1991  Ozaki ................................... 378/18

Primary Examiner—David P. Porta
Assistant Examiner—Don Wong
Attorney, Agent, or Firm—Quarles & Brady

[57] ABSTRACT

An x-ray CT system acquires scout data over a region of a patient prior to performing a scan. The scout data is employed to locate the patient in a succession of slices over the region. Geometric scan parameters including display field of view (DFOV), scan field of view (SFOV) and patient centering offsets ($X_{OFF}, Y_{OFF}$) are calculated from the scout data, displayed to the operator, and used as default values in the subsequent scan of the region.

5 Claims, 3 Drawing Sheets

AUTOMATIC FIELD OF VIEW AND PATIENT CENTERING DETERMINATION FROM PRESCAN SCOUT DATA

BACKGROUND OF THE INVENTION

The present invention relates to computed tomography (CT) imaging apparatus; and more particularly, to the automatic determination of scan field of view, display field of view, and patient centering parameters prior to a scan.

In a computed tomography system, an x-ray source projects a fan-shaped beam which is collimated to lie within an X–Y plane of a Cartesian coordinate system, termed the "imaging plane." The x-ray beam passes through the object being imaged, such as a medical patient, and impinges upon an array of radiation detectors. The intensity of the transmitted radiation is dependent upon the attenuation of the x-ray beam by the object and each detector produces a separate electrical signal that is a measurement of the beam attenuation. The attenuation measurements from all the detectors are acquired separately to produce the transmission profile.

The source and detector array in a conventional CT system are rotated on a gantry within the imaging plane and around the object so that the angle at which the x-ray beam intersects the object constantly changes. A group of x-ray attenuation measurements from the detector array at a given angle is referred to as a "view" and a "scan" of the object comprises a set of views made at different angular orientations during one revolution of the x-ray source and detector. In a 2D scan, data is processed to construct an image that corresponds to a two dimensional slice taken through the object. The prevailing method for reconstructing an image from 2D data is referred to in the art as the filtered backprojection technique. This process converts the attenuation measurements from a scan into integers called "CT numbers" or "Hounsfield units", which are used to control the brightness of a corresponding pixel on a cathode ray tube display.

Prior to a scan the operator typically enters a number of scan parameters that affect the location and quality of the reconstructed image. These include such geometric scan parameters as the scan field of view ("SFOV"), the display field of view ("DFOV") and patient centering parameters $X_{off}$ and $Y_{off}$.

The corrections made during reconstruction (often called the beam hardening coefficients) are dependent on the SFOV for the scan. Large, medium, and small SFOVs have different correction coefficients that are optimized for patients up to 48 cm, 35 cm, and 25 cm respectively. The DFOV is the region within the SFOV that is to be reconstructed. Generally the DFOV should be as small as possible and should be centered over the anatomy of interest. This results in the largest image for the anatomy of interest. Because a CT system normally projects maximum X-ray signal at the center of the SFOV, it is desirable to carefully center the patient within this region to obtain optimum image quality. Any residual mis-centering requires offsets in X and Y to position the smallest possible DFOV for the anatomy of interest within the SFOV.

Quite often the operator does not adjust these geometric parameters prior to each scan to optimize performance. This may occur because the operator does not have the necessary information upon which to base such settings, or because the time is simply not taken to determine the proper settings and make them. In any event, less than optimal images are often the result.

SUMMARY OF THE INVENTION

The present invention is a method for automatically setting the geometric scan parameters for a CT system prior to the acquisition of attenuation data from which an image is reconstructed. More specifically, the present invention includes acquiring scout data which indicates the attenuation profile of a patient at two orthogonal views, calculating the center of the attenuation profile from the two orthogonal views, calculating the offset ($Y_{OFF}$, $X_{OFF}$) of the attenuation profile center from the isocenter of the CT system, calculating the radius of the scan field of view (SFOV) as the distance between the isocenter and an edge of the attenuation profile, and calculating the radius of the display field of view (DFOV) as the distance between the attenuation profile center and the edge of the attenuation profile.

A general object of the invention is to automatically calculate the geometric scan parameters at the beginning of each scan. Orthogonal scout views are quickly obtained over a range which spans the locations from which slice images are to be acquired and reconstructed. The scan parameters $Y_{OFF}$, $X_{OFF}$, SFOV and DFOV are calculated from the scout data at each slice location, or range of slice locations, and these serve as default values that are used in the subsequent scan unless the operator overrides them.

A more specific object of the invention is to provide geometric scan parameters that are used in the subsequent scan. The SFOV parameter is used during the scan to determine the correction coefficients used to correct the attenuation data obtained from patients of varying sizes. The $Y_{OFF}$, $X_{OFF}$ values may be used to warn the operator that the patient is not properly positioned, and the $Y_{OFF}$ value may be used to set the patient table height.

DESCRIPTION OF THE PREFERRED EMBODIMENT

Figure 1:
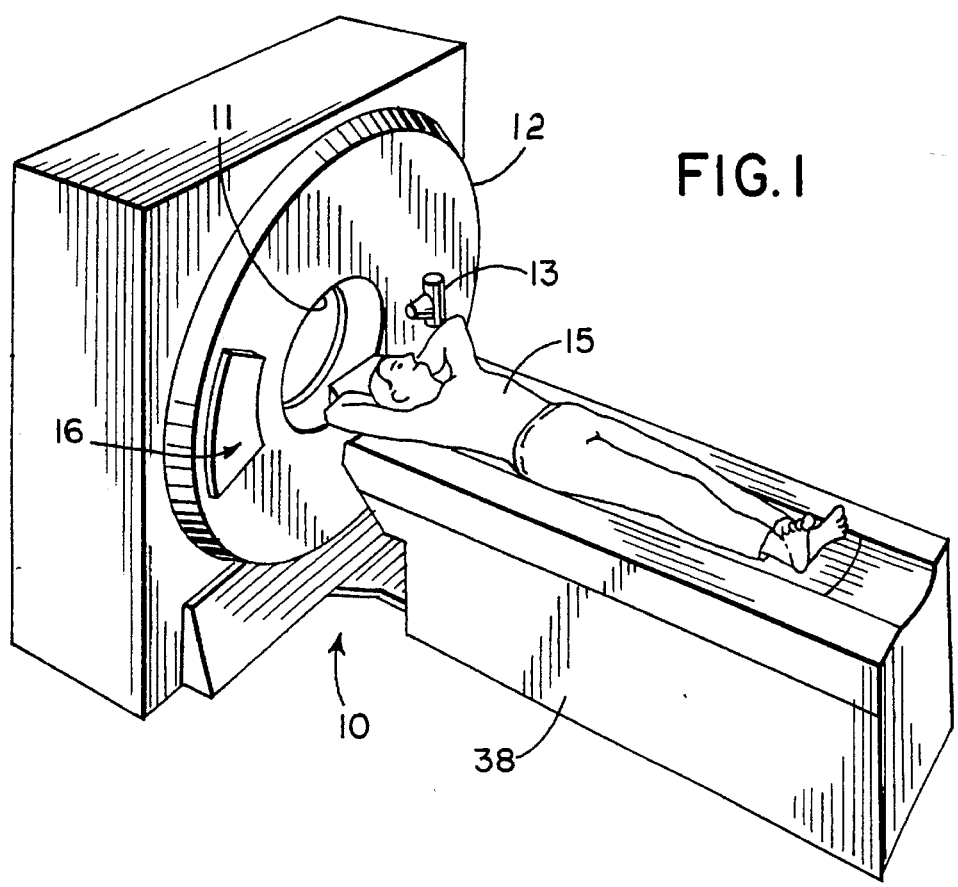
FIG. 1 is a pictorial view of a CT imaging system in which the present invention may be employed.
Figure 2:
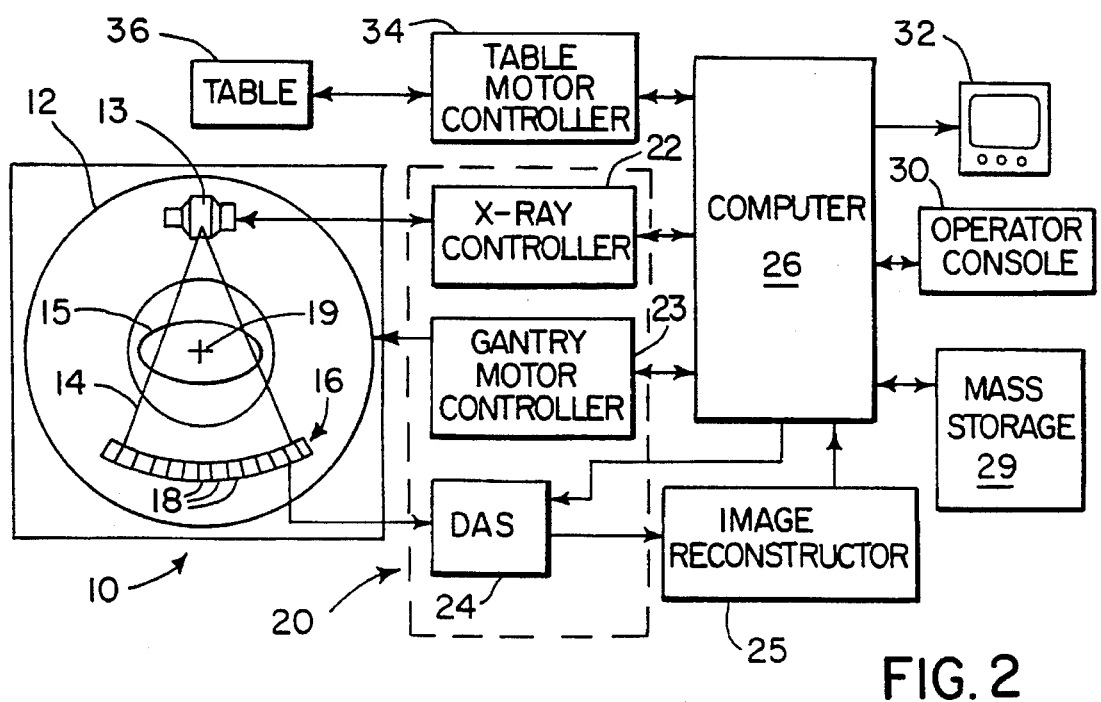
FIG. 2 is a block schematic diagram of the CT imaging system.

With initial reference to FIGS. 1 and 2, a computed tomography (CT) imaging system 10 includes a gantry 12 representative of a "third generation" CT scanner. Gantry 12 has an x-ray source 13 that projects a cone beam of x-rays 14 toward a detector array 16 on the opposite side of the gantry. The detector array 16 is formed by a number of detector elements 18 which together sense the projected x-rays that pass through a medical patient 15. Each detector element 18 produces an electrical signal that represents the intensity of an impinging x-ray beam and hence the attenuation of the beam as it passes through the patient. During a scan to acquire x-ray projection data, the gantry 12 and the components mounted thereon rotate about a center of rotation 19 located within the patient 15.

The rotation of the gantry and the operation of the x-ray source 13 are governed by a control mechanism 20 of the CT system. The control mechanism 20 includes an x-ray controller 22 that provides power and timing signals to the x-ray source 13 and a gantry motor controller 23 that controls the rotational speed and position of the gantry 12. A data acquisition system (DAS) 24 in the control mechanism 20 samples analog data from detector elements 18 and converts the data to digital signals for subsequent processing. An image reconstructor 25, receives sampled and digitized x-ray data from the DAS 24 and performs high speed image reconstruction according to the method of the present invention. The reconstructed image is applied as an input to a computer 26 which stores the image in a mass storage device 29.

The computer 26 also receives commands and scanning parameters from an operator via console 30 that has a keyboard. An associated cathode ray tube display 32 allows the operator to observe the reconstructed image and other data from the computer 26. The operator supplied commands and parameters are used by the computer 26 to provide control signals and information to the DAS 24, the x-ray controller 22 and the gantry motor controller 23. In addition, computer 26 operates a table motor controller 34 which controls a motorized table 36 to position the patient 15 in the gantry 12.

Figure 3:
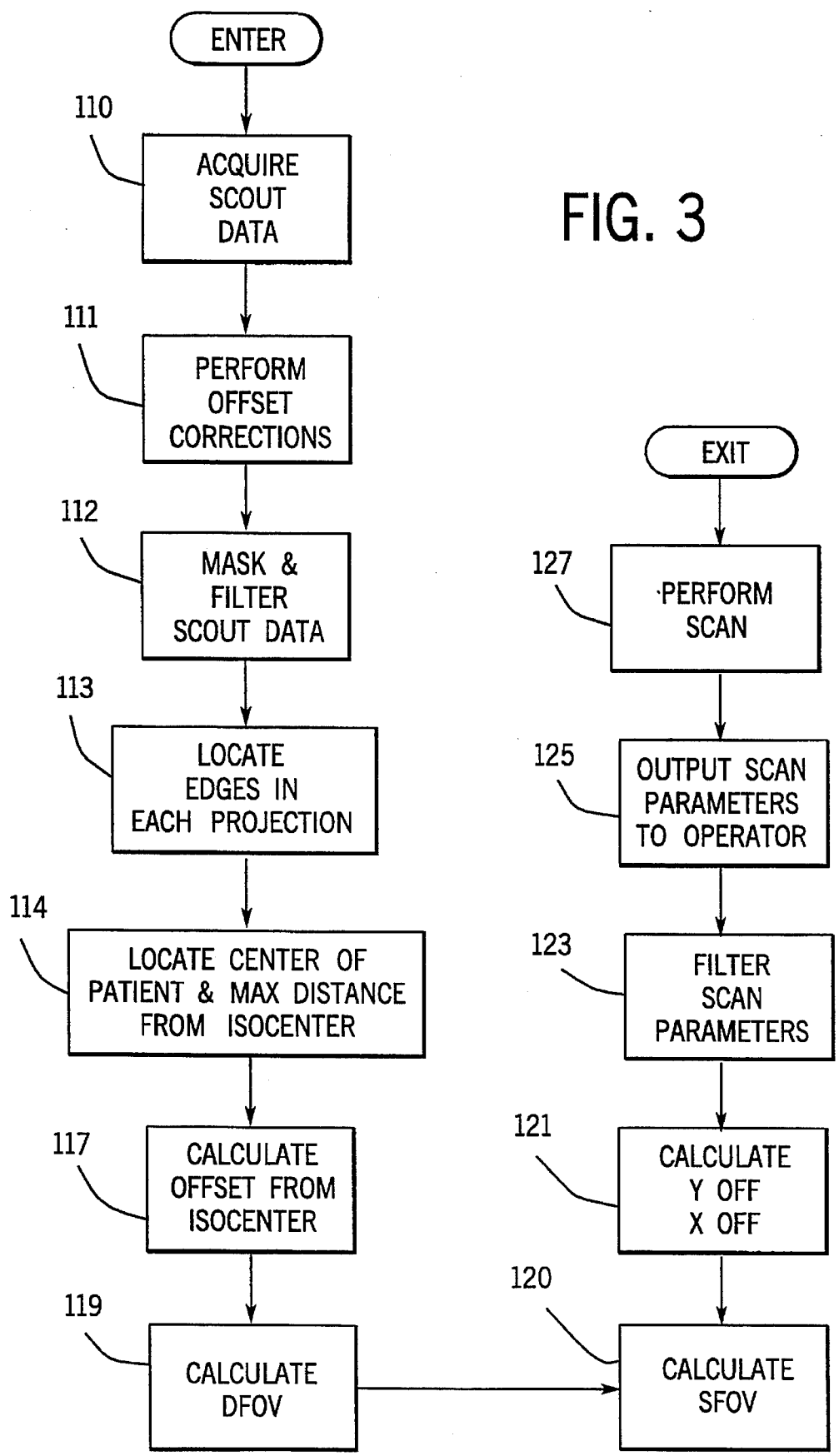
FIG. 3 is a flow chart of the process carried out by the CT imaging system of FIG. 2 to practice the preferred embodiment of the invention.
Figure 4:
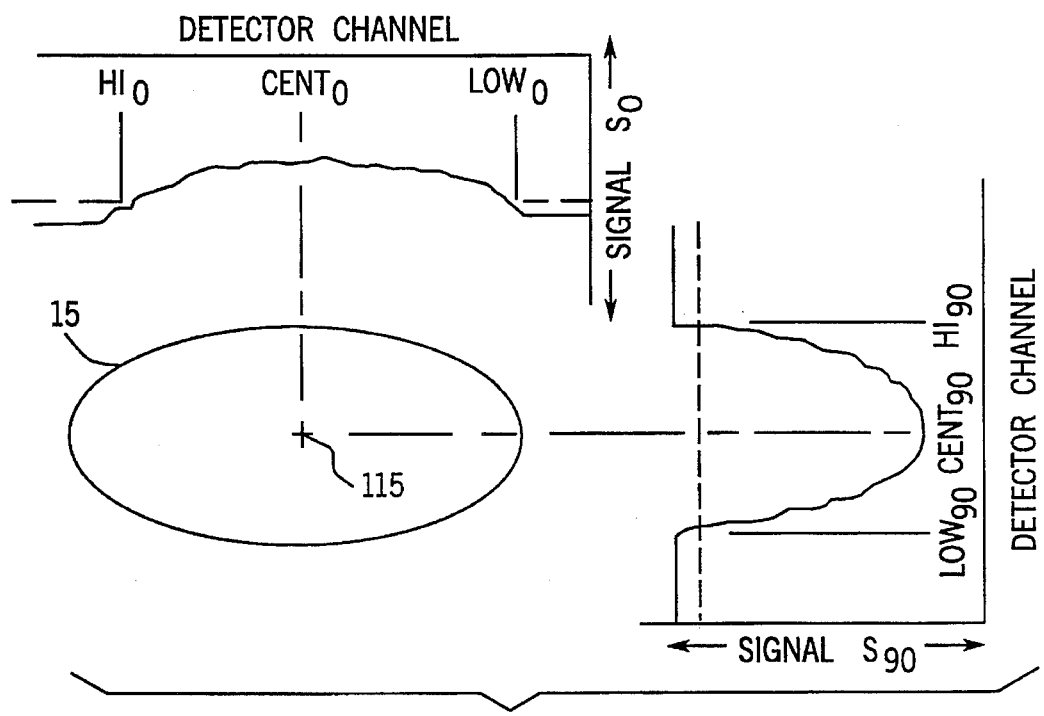
FIG. 4 is a graphic representation of scout data acquired as part of the present invention.

Referring particularly to FIG. 2, the computer 26 directs the system components to carry out the prescribed scan in accordance with stored programs. The program illustrated by the flow chart in FIG. 3 is executed by computer 26 to implement the preferred embodiment of the present invention. The first step is to acquire scout data, as indicated at process block 110. As illustrated in FIG. 4, this scout data is comprised of two orthogonal views from each slice position in the prescribed scan, one at a gantry angle of 0° and the other at an angle of 90°.

As indicated at process block 111, the usual corrections are made to the acquired scout data $S_0$ and $S_{90}$ to correct for offsets and to normalize to a reference detector. The projections are then filtered at process block 112. This filtering includes masking out attenuation due to undesired objects such as the patient table, followed by low pass filtering the scout projection data using an 11 point box car filter.

As indicated at process block 113, the edges of the patient are then located in each scout projection. The attenuation data for each detector element (i) in the projection is compared to a threshold (thresh=1.5) and the lowest detector [$low_0$ and $low_{90}$] and the highest detector [$high_0$ and $high_{90}$] located at the ends of the longest contiguous string of readings above the threshold are selected as shown in FIG. 4. As indicated by process block 114 and shown in FIG. 4, the center 115 of the patient 15 is then located in each projection:

$$cent_0 = \frac{Hi_0 + Low_0}{2}$$

$$cent_{90} = \frac{Hi_{90} + Low_{90}}{2}$$

Figure 5:
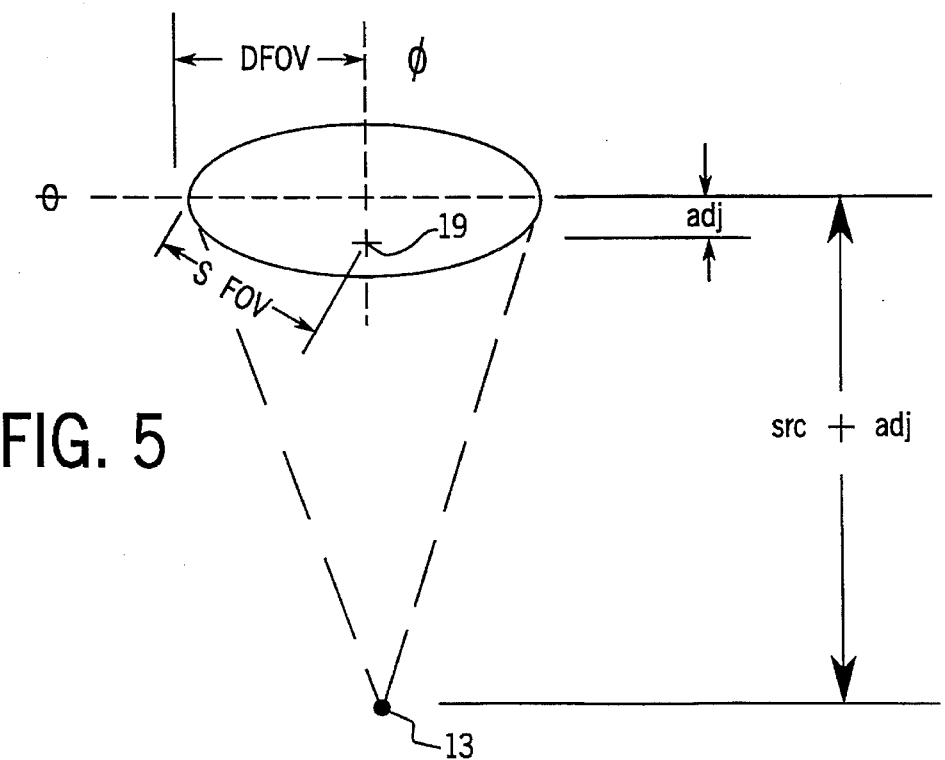
FIG. 5 is a schematic representation of the imaging plane used to explain the calculations carried out by the preferred embodiment of the invention.

The same edges are used to determine the edge which is furthest from the isocenter 19 in each projection.

cdet=isocenter detector element if $cdet-low_0 > hi_0 - cdet$ then $max_{13}rad_0 = cdet-low_{90}$ else $max_{13}rad_{90} = hie-cdet$ if $cdet-low_{90} > hi_{90}-cdet$ then $max_{13}rad_{90} = cdet-low_{90}$ else $max_{13}rad_{90} = hi_{90}-cdet$ As indicated by process block 117 and illustrated in FIG. 5 the next step is to determine the distance "adj" between the patient center $cent_0$ or $cent_{90}$ and the isocenter, cdet, as measured in the narrower of the two orthogonal projections.

$sep_0 = hi_0 - low_0$ $sep_{90} = hi_{90} - low_{90}$ if $sep_0 > sep_{90}$ then $\phi=0$ and $\theta=90$ else $\phi=90$ and $\theta=0$.

$adj=(sgn_\theta)(src)(tan(cent\theta-cdet)(pitch))$ where src=distance in cm form x-ray source 13 to isocenter 19;

pitch=angle between detector elements 18 in degrees;

$sgn_O=-1$ or $sgn_{90}=1$.

Referring still to FIGS. 3 and 5, the radius of the display field of view DFOV can now be calculated as indicated at process block 119. This is the distance between the patient center $cent_0$ or $cent_{90}$ and the most remote edge of the patient and is calculated as follows:

$DFOV=(src+adj)(tan((sep_{100}/2)(pitch)))$.

As indicated at process block 120, the radius of the scan field of view SFOV is then calculated. This is the distance between the system isocenter 19 and the most remote edge of the two orthogonal projections:

$SFOV=(src+adj)(tan((max\_rad\phi)(pitch)))$.

As indicated at process block 121 the x and y offsets $X_{OFF}$ and $Y_{OFF}$ are then calculated. These are the distances between the system isocenter 19 and the center of the patient along the respective horizontal and vertical axes:

$Y_{OFF}=(sgn_{90})(src)(tan((cent_{90}-cdet)(pitch)))$ $X_{OFF}=(sgn_0)(src)(tan((cent_0-cdet)(pitch)))$ In a typical scout scan the two orthogonal scout projections are acquired at a succession of slice locations along the z axis over the entire anatomy to be imaged. These samples may be spaced apart 1 mm and as many as 250 separate values for DFOV, SFOV, $X_{OFF}$ and $Y_{OFF}$ are produced by the above process. While these geometric scan parameters could be used directly to change the set-up for each separate slice designated by the operator, in the preferred embodiment a single value for each parameter is output to the operator for use over the entire range of selected slices.

Referring again to FIG. 4, the geometric scan parameters over the selected range of slices to be imaged are first filtered as indicated by process block 123. A low pass filter such as a 5 point box car filter is used to remove high frequency variations in the value of each parameter over the selected z axis range. As indicated at process block 125 the mean value of each set of filtered parameters SFOV, DFOV, $X_{OFF}$ and $Y_{OFF}$ are then output to the operator and become the default set-up for the scan which is subsequently performed at 127. Since centering of the patient about the system isocenter 19 is an important factor in image quality, it is contemplated that the operator may choose to change the table height before conducting the scan if the vertical offset $Y_{OFF}$ is excessive. In the past centering along the horizontal axis has not been a problem for operators and $X_{OFF}$ will usually be minimal and not require repositioning of the patient.

I claim:

1. A method for determining geometric scan parameters prior to scanning a patient with an x-ray CT system, the steps comprising:

acquiring scout data which indicates patient attenuation of x-rays at two substantially orthogonal views;

locating the edges of the patient in each view by comparing said scout data with a preset threshold;

locating the center of the patient in each view by calculating the midpoint between the located edges;

calculating the display field of view (DFOV) measured from the center of the patient to the most distant located edge of the patient;

calculating the scan field of view (SFOV) measured from a CT system isocenter to the most distant located edge of the patient;

calculating the patient offsets ($Y_{OFF}$ and $X_{OFF}$) measured from the CT system isocenter to the located center of the patient; and outputting as the geometric scan parameters the calculated values of DFOV, SFOV, $Y_{OFF}$ and $X_{OFF}$ scanning the patient based on the output geometric scan parameters.

2. The method as recited in claim 1 in which the acquired scout data is corrected and low-pass filtered prior to locating said edges.

3. The method as recited in claim 1 in which scout data is acquired over a region of the patient and a plurality of pairs of substantially orthogonal views are produced at successive slice locations through the patient.

4. The method as recited in clam 3 in which values for DFOV, SFOV, $X_{OFF}$ and $Y_{OFF}$ are calculated at said successive slice locations.

5. The method as recited in claim 4 in which the geometric scan parameters which are output are the mean value of the respective DFOV, SFOV $X_{OFF}$ and $Y_{OFF}$ values calculated at successive slice locations.

* * * * *